United States Patent [19]

Burke

[11] Patent Number: 5,620,678
[45] Date of Patent: Apr. 15, 1997

[54] WATER-SOLVENT-BASED AEROSOL INSECTICIDE

[75] Inventor: Terrence R. Burke, St. Louis County, Mo.

[73] Assignee: S. C. Johnson & Son, Inc., Racine, Wis.

[21] Appl. No.: 653,751

[22] Filed: May 31, 1996

Related U.S. Application Data

[63] Continuation of Ser. No. 377,664, Jan. 23, 1995, abandoned, which is a continuation of Ser. No. 53,320, Apr. 26, 1993, abandoned, which is a continuation of Ser. No. 689,180, Apr. 22, 1991, abandoned.

[51] Int. Cl.$^6$ ..................................... A01N 25/06
[52] U.S. Cl. ............................... 424/45; 424/405
[58] Field of Search ..................... 424/43, 45, 46, 424/47, 405; 514/65, 772, 789, 75

[56] References Cited

U.S. PATENT DOCUMENTS

| | | | |
|---|---|---|---|
| 2,358,986 | 9/1944 | McGovran et al. | 424/45 |
| 3,207,386 | 9/1965 | Presant et al. | 222/394 |
| 4,041,148 | 8/1977 | Simons et al. | 424/45 |
| 4,139,607 | 2/1979 | Simons et al. | 424/45 |
| 4,160,336 | 7/1979 | Query et al. | 43/132 A |
| 4,187,204 | 2/1980 | Howard | 260/22 |
| 4,381,066 | 4/1983 | Page et al. | 222/394 |
| 4,384,661 | 5/1983 | Page et al. | 222/394 |
| 4,420,575 | 12/1983 | Rapaport et al. | 523/504 |
| 4,439,343 | 3/1984 | Albanese | 252/305 |
| 4,439,344 | 3/1984 | Albanese | 252/312 |
| 4,444,745 | 4/1984 | Jacobson et al. | 424/45 |
| 4,450,151 | 5/1984 | Shinozawa | 424/45 |
| 4,450,253 | 5/1984 | Sulk | 524/378 |
| 4,483,783 | 11/1984 | Albanese | 252/312 |
| 4,487,334 | 12/1984 | Werding | 222/55 |
| 4,534,128 | 8/1985 | Query et al. | 43/132.1 |
| 4,595,679 | 6/1986 | Broadbent | 514/67 |
| 4,597,895 | 7/1986 | Bartlett | 252/392 |
| 4,600,530 | 7/1986 | Bartlett | 252/392 |
| 4,604,226 | 8/1986 | Bartlett | 252/389 A |
| 4,624,070 | 11/1986 | Query et al. | 43/132.1 |
| 4,668,507 | 5/1987 | Tomkins et al. | 424/45 |
| 4,822,613 | 4/1989 | Rodero | 424/405 |
| 4,826,674 | 5/1989 | Albanese | 424/45 |
| 4,889,710 | 12/1989 | Hagarty | 424/45 |
| 4,904,464 | 2/1990 | Albanese | 424/45 |
| 5,055,299 | 10/1991 | Domara et al. | 424/405 |
| 5,104,658 | 4/1992 | Hagarty | 424/405 |

OTHER PUBLICATIONS

Description and properties of "Propoxur", *The Merck Index, Ninth Edition*, Merck & Co., Inc., Rahway, NJ, (1976), p. 1015.

Description and properties of "Carbaryl", Update 5—Jun. 1986 of *The Agrochemicals Handbook* of the Royal Society of Chemistry, University of Nottingham, England, 2 pages dated AO57/Jun. 85.

The AgroChemicals Handbook—Acephate 1983—The Royal Society of Chemistry.

*Primary Examiner*—Neil S. Levy
*Attorney, Agent, or Firm*—R. E. Rakoczy; J. W. Frank

[57] ABSTRACT

A water-based or solvent-based, or combinations thereof, aerosol insecticide is provided. Dimethylether (DME) is used both as a solvent and a propellant. The DME holds the ingredients of the aerosol in a homogenous liquid solution while it is in an aerosol bomb. Upon release of the aerosol, the DME flashes off and the remaining ingredients separate into two phases: a liquid phase, and a solid or oil phase having the active insecticidal ingredients.

9 Claims, No Drawings

WATER-SOLVENT-BASED AEROSOL INSECTICIDE

This application is a continuation of application Ser. No. 08/377,664 filed on Jan. 23, 1995, now abandoned, which is a continuation of U.S. Ser. No. 08/053,320 filed on Apr. 26, 1993, abandoned, which is a continuation of U.S. Ser. No. 07/689,180 filed on Apr. 22, 1991, abandoned.

BACKGROUND OF THE INVENTION

This invention relates to insecticides, and, in particular, to novel formulations for the efficacious delivery of pesticides, water or solvent based insecticides which will not harm the ozone layer of the atmosphere when released.

Halogenated solvents, such as methylene chloride and 1,1,1-trichloroethane are common carriers, diluents and solvents for aerosol sprays. However, they have been restricted due to health and environmental concerns. To alleviate these concerns, many aerosol manufacturers shifted from solvent-based aerosols to water-based aerosols. Many of these aerosols used water as a carrier, dimethylether (DME) as a propellant, and a solvent. The use of DME as a propellant is well known. See for example U.S. Pat. No. 2,358,986 to McGovran et al. Because the insecticide is emulsified in the water, the prior art water-based aerosol insecticides do not have a sustaining good knock-down effect, and when sprayed on a porous surface, such as wood or drywall, the insecticide is significantly absorbed by the surface. As a result, the remaining solvent has a tendency to dilute the insecticide. Thus, consequently, there is not enough insecticide on the surface in sufficient toxic amount to be available for insects to receive in the required amount to effectively kill the same. None of the prior art insecticides disclose a formula wherein the active insecticidal agents are separated from the water or diluent upon release from the aerosol can in order to avoid the problem of dilution, absorbtion and slow knockdown. See for example U.S. Pat. No. 2,358,986 to McGovran et al.; U.S. Pat. No. 4,439,342; U.S. Pat. No. 4,439,343; U.S. Pat. No. 4,439,344; U.S. Pat. No. 4,483,783; and U.S. Pat. No. 4,826,674, all to Albanese; U.S. Pat. No. 4,487,334 to Werding; and, U.S. Pat. No. 4,381,066 and U.S. Pat. No. 4,384,661, both to Page et al.; U.S. Pat. No. 4,187,204 to Howard; U.S. Pat. No. 4,420,575 to Rapaport et al.; U.S. Pat. No. 4,450,253 to Suk; U.S. Pat. No. 3,207,386 to Presant et al.; and, U.S. Pat. No. 4,041,148 and U.S. Pat. No. 4,139,607, both to Simons et al.

SUMMARY OF THE INVENTION

One object of the present invention is to provide an effective, yet environmentally safe insecticide formulation.

Another object of this invention is to provide such an insecticide formulation which has good knock-down and kill capabilities for flying and crawling insects.

A further object of this invention is to provide such results that the target insects will be exposed to the undiluted insecticide which will remain on the surface upon which it is sprayed without being absorbed by such surface.

Other objects of this invention will be apparent to those skilled in the art in light of the following description.

In accordance with this invention, generally stated, there is provided a water-based or solvent-based insecticide formulation in an aerosol, the insecticide comprises a diluent, at least one active insecticidal ingredient which is insoluble in the diluent, and dimethylether. The diluent is chosen from the group consisting of water and petroleum distillates, which can include isoparaffinic hydrocarbons, or other solvent or diluents in which the active component is not soluble. The dimethylether is a co-solvent which holds the active ingredients in solution with the diluent so that the insecticide is maintained as a homogenous liquid solution within the aerosol can. Upon releasing the insecticide, the dimethylether flashes and a two phase system forms, one phase comprising the diluent, and a second phase comprising said insecticidal ingredients.

The formulation insecticide may include a co-solvent to make production of the aerosol easier. The co-solvent is preferably chosen from the group consisting of isopropyl alcohol, 1-methyl-2-pyrrolidinone, and combinations thereof. Obviously, other equivalent co-solvents may work just as effectively.

The natural physical state of the active insecticidal ingredients are preferably a solid or an oil when not in solution. If the insecticide is to be used to kill crawling insects, the active ingredients can be chosen from any group including organophosphates, carbamates, and pyrethroids, such as chlorpyrifos, propoxur, or cypermethrin, as examples. If the insecticide is to combat flying insects, the active ingredients are preferably chosen from the group consisting of natural pyrethrum, synthetic pyrethroids, and combinations thereof.

The flying insect insecticide may include synergistic agents. The synergistic agents preferably are chosen from the group consisting of piperonyl butoxide, N-octyl bicycloheptene dicarboximide and combinations thereof, while many other like agents are readily commercially available.

The aerosol may include corrosion inhibitors chosen from any group including oleamide DEA, phosphate esters, sodium benzoate and sodium nitrate.

As can be obvious from that as reviewed herein, the concept of this invention is not only to provide a water-based insecticide, but an insecticide that may be water-based, or solvent-based, or a combination thereof, and emplaced within an aerosol can, so as to remain miscible within the solvent within the can, until sprayed. Such is the concept of the invention herein. The mixing of the insecticide with dimethylether, and a co-solvent, becomes a homogeneous mixture within the solvent in the can. When sprayed, the water or other solvents available dissipate, leaving the undiluted insecticide on the surface of the area sprayed or undiluted insecticide suspended in the air.

DESCRIPTION OF THE PREFERRED EMBODIMENT

The use of dimethylether (DME) as a propellant has been known for some time. However, it is also a strong polar solvent which has been found to be able to hold active insecticidal ingredients in solution with a diluent while in an aerosol bomb (i.e. in an aerosol can). It has also been found that when the aerosol is released (discharged) the DME flashes off, allowing the insecticidal ingredients and the diluent to separate into two phases; the diluent being one phase, the insecticide being the other. This allows the insecticide to return to its natural physical state upon release, i.e., if the insecticide is naturally a crystal, it will crystallize upon release. Because the insecticide is separate from the diluent, it will not be absorbed into the contacted porous surfaces. Therefore, there is more insecticide available for insects to ingest, and the insecticide is thus more effective in application.

The aerosol is preferably made by combining the insecticidal agents and a corrosion inhibitor and dissolving them in isopropyl alcohol. Water is added next and then DME. The corrosion inhibitor is added to protect the aerosol can from corrosion which would otherwise occur due to the can's contact with the water ingredient.

The aerosol could be made without the use of the isopropyl alcohol, which only acts as a co-solvent. However, the use of isopropyl alcohol makes production easier and is thus preferred.

The following examples show various formulations of insecticidal aerosols made in accordance with the above procedure.

| Crawling Insect Insecticides | | |
|---|---|---|
| Example I | | |
| 0.505% | Chlorpyrifos* | insecticide |
| 10.000% | Isopropyl alcohol | co-solvent |
| 0.300% | Oleamide DEA | corrosion inhibitor |
| 59.195% | Deionized water | diluent |
| 30.000% | DME | solvent/propellent |

*O,O-diethyl O-(3,5,6-trichloro-2-pyridinyl) phosphorothioate available from Dow Chemical U.S.A. under the trademark Dursban R 99%

| Example II | | |
|---|---|---|
| 0.505% | Chlorpyrifos | insecticide |
| 4.000% | Isopropyl alcohol | co-solvent |
| 0.300% | Oleamide DEA | corrosion inhibitor |
| 65.195% | Deionized water | diluent |
| 30.000% | DME | solvent/propellent |

| Example III | | |
|---|---|---|
| 1.087% | Propoxur* | insecticide |
| 10.000% | Isopropyl alcohol | co-solvent |
| 0.300% | Oleamide DEA | corrosion inhibitor |
| 58.613% | Deionized water | diluent |
| 30.000% | DME | solvent/propellent |

*2-(1-methylethoxy)phenol methylcarbamate available from the Agricultural Chemicals Division of Mobay Chemical Corporation under the trademark Baygon, technical.

Because the DME flashes upon release from the aerosol can, chlorpyrifos and propoxur, which are both solid, crystalline insecticides, recrystallize immediately upon release from the aerosol bomb. As they are not held in solution or dissolved in the water after release, the insecticide will remain on the surface upon which it is sprayed. It will not be absorbed into the surface to any appreciable extent. Thus, there is more crystalized insecticide readily available for insects to ingest or otherwise contact.

| Flying Insect Insecticide | | |
|---|---|---|
| Example IV | | |
| 1.250% | Pyrethrum, technical | insecticide |
| 0.278% | d-trans Allethrin | pyrethroid insecticide |
| 1.000% | MGK-264* | synergist |
| 1.000% | Piperonyl Butoxide | synergist |
| 18.000% | Isopropyl alcohol | co-solvent |
| 0.300% | Oleamide DEA | corrosion inhibitor |
| 33.172% | Deionized water | diluent |
| 45.000% | DME | solvent/propellent |

*MGK-264: McLaughlin Gormley King Co. trademark for N-octyl bicycloheptene dicarboximide

| Example V | | |
|---|---|---|
| 1.183 | Resmethrin* | pyrethroid insecticide |
| 1.000 | M-Pyrol** | co-solvent |
| 10.000% | Isopropyl alcohol | co-solvent |
| 0.250% | Oleamide DEA | corrosion inhibitor |

| Flying Insect Insecticide | | |
|---|---|---|
| 42.567% | Deionized water | diluent |
| 45.000% | DME | solvent/propellent |

*(5-Benzyl-3-fury)methyl-2,2-dimethyl-3-(2-methylpropenyl) cyclopropanecarboxylate, available from S.B. Benick and Company under the Trademark SBP-1382.
**Trademark of GAF Chemicals Corp for N-methylpyrrolidinone.

Example IV includes synergistic agents to help increase the efficacy of the insecticides. In both Example IV and V, the insecticides and synergistic agents are all liquid oils, except that Resmethrin crystals are present as the insecticide. Upon dispensing, they form a highly atomized fog. The crawling insect formulae (Examples I–III) have a lower percentage of DME than the flying insect formulae. The lower percentage of DME in the crawling insect formulae reduces the amount of atomization. A high degree of atomization is not required for crawling insects because it is not desirable to spray a large area. It is preferable to concentrate the insecticide in the immediate area of the insect to be sprayed, or in proximity therewith.

| Example VI | | |
|---|---|---|
| 3.080% | Orthene Tech, 97% | insecticide |
| 10.000% | Isopropyl alcohol | co-solvent |
| 36.920% | Isopar L* | diluent |
| 50.000% | DME | solvent/propellant |

*A trademark of Exxon Company U.S.A., a division of Exxon Corporation for a hydrotreated heavy naptha, petroleum consisting primarily of $C_{11}$–$C_{13}$ isoparaffinic hydrocarbons.

In this example, Isopar L, an isoparaffin petroleum distillate operates in the same manner as the water in the preceeding examples. The combination of the co-solvents, and the solvent/propellant, together make a homogeneous mixture within the can, in order to sustain the dilution of the mixture within the container, until sprayed.

Numerous variations, within the scope of the appended claims, will be apparent to those skilled in the art in light of the foregoing description and accompanying drawings.

Having thus described the invention, what is claimed and desired to be secured by Letters Patent is:

1. A solvent-based aerosol insecticidal composition to be sprayed upon an insect that is embodied in a homogeneous liquid solution contained under pressure in an aerosol can which solution becomes a two-phase system upon release from the aerosol can, the insecticidal composition being produced by a method comprising:

placing in the aerosol can at least one active insecticidal ingredient selected from the group consisting of organophosphates and a co-solvent which dissolves the insecticidal ingredient and maintains the insecticidal ingredient in solution while it is contained in the aerosol can;

adding a diluent to said at least one insecticidal ingredient and co-solvent, said at least one insecticidal ingredient being insoluble in said diluent, said diluent being a hydrocarbon solvent;

adding dimethyl ether as a propellant and a solvent under pressure, said dimethyl ether holding said insecticidal ingredient, co-solvent and said diluent in a homogeneous liquid solution within the aerosol can and said insecticidal ingredient is a solid or an oil when not in solution; and whereby upon releasing the aerosol insecticide, the dimethyl ether and co-solvent present flash, and the two-phase system forms, one phase comprising the diluent which separates, and a second phase comprising said insecticidal ingredient, said insecticidal ingredient returning to its solid or oil state when it separates from the diluent;

wherein the insecticidal composition consists essentially of organophosphate active insecticidal ingredient in the range of 0.01%–10.0%, co-solvent in the range of up to 25%, diluent in the range of 25.0%–90.0%, and dimethyl ether in the range of 10.0%–75.0%.

2. The insecticidal composition of claim 1 wherein the co-solvent is selected from the group consisting of isopropyl alcohol, 1-methyl-2-pyrrolidone, and combinations thereof.

3. The insecticidal composition of claim 1 wherein the insecticidal ingredient is acephate.

4. The insecticidal composition of claim 2 wherein the insecticidal ingredient is acephate.

5. The insecticidal composition of claim 1 wherein the diluent is an isoparaffinic hydrocarbon.

6. The insecticidal composition of claim 2 wherein the diluent is an isoparaffinic hydrocarbon.

7. The insecticidal composition of claim 1 wherein the diluent is an isoparaffinic hydrocarbon and the insecticidal ingredient is acephate.

8. The insecticidal composition of claim 7 wherein the co-solvent is selected from the group consisting of isopropyl alcohol, 1-methyl-2-pyrrolidone, and combinations thereof.

9. The insecticidal composition of claim 7 wherein the co-solvent is isopropyl alcohol.

\* \* \* \* \*